United States Patent
Stanley et al.

(10) Patent No.: US 6,414,205 B1
(45) Date of Patent: Jul. 2, 2002

(54) PROCESS FOR THE REMOVAL OF MAPD FROM HYDROCARBON STREAMS

(75) Inventors: Stephen J. Stanley, Matawan, NJ (US); Gary R. Gildert, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 09/534,279

(22) Filed: Mar. 24, 2000

(51) Int. Cl.[7] .......................... C07C 7/167; C07C 5/02; C07C 29/80

(52) U.S. Cl. .................. 585/259; 585/260; 585/264; 585/265; 203/DIG. 6; 203/84; 203/19

(58) Field of Search ................ 585/254, 260, 585/264, 265; 203/DIG. 6, 84, 19

(56) References Cited

U.S. PATENT DOCUMENTS

| | | | |
|---|---|---|---|
| 3,770,619 A | * 11/1973 | Derrien et al. | 208/255 |
| 4,232,177 A | 11/1980 | Smith, Jr. | 585/324 |
| 4,302,356 A | 11/1981 | Smith, Jr. | 252/426 |
| 4,443,559 A | 4/1984 | Smith, Jr. | 502/527 |
| 4,447,668 A | 5/1984 | Smith, Jr. et al. | 585/639 |
| 4,982,022 A | 1/1991 | Smith, Jr. et al. | 568/899 |
| 5,019,669 A | 5/1991 | Adams et al. | 585/446 |
| 5,240,568 A | * 8/1993 | Chan et al. | 203/84 |
| 5,321,163 A | 6/1994 | Hickey et al. | 568/59 |
| 5,431,890 A | 7/1995 | Crossland et al. | 422/211 |
| 5,595,634 A | 1/1997 | Hearn et al. | 203/29 |
| 5,730,843 A | 3/1998 | Groten et al. | 202/158 |
| 5,877,363 A | 3/1999 | Gildert et al. | 585/260 |
| 6,084,140 A | * 7/2000 | Kitamura et al. | 585/260 |

FOREIGN PATENT DOCUMENTS

| | | |
|---|---|---|
| GB | 835689 | 5/1960 |
| WO | WO 95/15934 | 6/1995 |

OTHER PUBLICATIONS

Gerd Kaibel, 1987, Chem Eng Technol 10, pp. 92–98.*

* cited by examiner

Primary Examiner—Thuan D. Dang
(74) Attorney, Agent, or Firm—Kenneth H. Johnson

(57) ABSTRACT

A process for the selective hydrogenation of the methyl acetylene and propadiene (MAPD) in a propylene rich stream is disclosed wherein the selective hydrogenation is carried out stepwise (a) first in a single pass fixed bed reactor and then (b) in a distillation column reactor containing a supported PdO hydrogenation catalyst which serves as a component of a distillation structure. Conversion and selectivity to propylene in improved over the use of the single pass fixed bed reactor alone.

7 Claims, 3 Drawing Sheets

PROCESS FOR THE REMOVAL OF MAPD FROM HYDROCARBON STREAMS

BACKGROUND OF THE INVENTION

1. Field of the Invention

The present invention relates to removal of MAPD from hydrocarbon streams. More particularly the invention relates to a process wherein the MAPD is converted to valuable propylene by selective hydrogenation. More particularly the invention relates to a process where one of the hydrogenation reactors is a distillation column reactor wherein the propylene is concurrently separated from a stream containing unconverted MAPD.

2. Related Information

Methyl acetylene/propadiene (MAPD) is not a compound but covers the unstable compounds methyl acetylene and propadiene which may be depicted as follows:

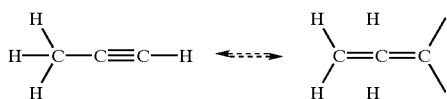

The MAPD compounds are highly reactive contaminants in a propylene stream. The most common method of removal is by selective hydrogenation which not only "removes" the contaminants but converts them to valuable product propylene. The propylene stream is then fractionated to remove a portion of the stream which contains unconverted MAPD. The stream containing the unconverted MAPD is called "Green Oil" and the fractionation tower used to separate the stream containing the unconverted MAPD from the propylene is called the "Green Oil Tower".

Prior methods of the selective hydrogenation of MAPD in propylene streams have used both liquid and vapor phase reactors. Generally while conversion is good, in both cases the selectivity drops off rapidly with time. Thus, it would be desirable to improve selectivity in general and keep the selectivity over time. Both the vapor phase and liquid phase system utilize at least two reactors in parallel, with sometimes three, leaving at least one spare for regeneration.

The main drawback of this method is that the selectivity to propylene is not always as desired. The by-product of the hydrogenation, however, is propane which is not considered a contaminant when further processing of the propylene is carried out. However, it does reduce the amount of valuable propylene produced.

The term "reactive distillation" is used to describe the concurrent reaction and fractionation in a column. For the purposes of the present invention, the term "catalytic distillation" includes reactive distillation and any other process of concurrent reaction and fractional distillation in a column regardless of the designation applied thereto.

A preferred catalytic distillation is one in which a distillation structure also serves as the catalyst for the reaction. The use of a solid particulate catalyst as part of a distillation structure in a combination distillation column reactor for various reactions is described in U.S. Pat. Nos. (etherification) 4,232,177; (hydration) 4,982,022; (dissociation) 4,447,668; (aromatic alkylation) 5,019,669 and (hydrogenation) 5,877,363. Additionally U.S. Pat. Nos. 4,302,356; 4,443,559; 5,431,890 and 5,730,843 disclose catalyst structures which are useful as distillation structures.

Hydrogenation is the reaction of hydrogen with a carbon-carbon multiple bond to "saturate" the compound. This reaction has long been known and is usually done at super atmospheric pressures and moderate temperatures using a large excess of hydrogen over a metal catalyst. Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al in "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", *Hydrocarbon Processing*, March 1985, presents a general, non enabling overview of various uses of hydrogenation catalysts, including selective hydrogenation of a propylene rich stream and other cuts. Conventional liquid phase hydrogenations as presently practiced required high hydrogen partial pressures, usually in excess of 200 psi and more frequently in a range of up to 400 psi or more. In a liquid phase hydrogenation the hydrogen partial pressure is essentially the system pressure.

UK Patent Specification 835,689 discloses a high pressure, concurrent trickle bed hydrogenation of $C_2$ and $C_3$ fractions to remove acetylenes. The selective hydrogenation of MAPD in propylene streams utilizing catalytic distillation alone is disclosed in International Application WO 95/15934.

It is an advantage of the present process that the propadiene and methyl acetylene contained within the hydrocarbon stream contacted with the catalyst are selectively converted to propylene with very little if any formation of oligomers or little if any saturation of the mono-olefins contained in the feed.

SUMMARY OF THE INVENTION

The present invention comprises the selective hydrogenation of methyl acetylene and propadiene (MAPD) contained within a propylene rich stream to purify the stream and obtain greater amounts of the propylene. In a class of preferred embodiments the propylene rich stream is fed along with hydrogen first to a standard single pass fixed bed reactor and the effluent then fed to a catalytic distillation column reactor and contacted with hydrogen in a reaction zone containing a hydrogenation catalyst, such as supported palladium oxide catalyst, preferably in the form of a catalytic distillation structure. The hydrogenation catalyst in the single pass fixed bed reactor may the same or different from that in the catalytic distillation column reactor. Hydrogen is provided as necessary to support the reaction and, it is believed, to reduce the oxide and maintain it in the hydride state. The distillation column reactor is operated at a pressure such that the reaction mixture is boiling in the bed of catalyst. If desired, a bottoms stream containing any higher boiling material (the Green Oil) may be withdrawn to effectuate a complete separation.

The single pass fixed bed reactor(s) may be any of those known in the art, as may the hydrogenation catalyst.

The hydrogen rate must be adjusted such that it is sufficient to support the hydrogenation reaction and replace hydrogen lost from the catalyst but kept below that required for hydrogenation of propylene and, in the case of the catalytic distillation reactor, to prevent flooding of the column which is understood to be the "effectuating amount of hydrogen" as that term is used herein. Generally the mole ratio of hydrogen to methyl acetylene and propadiene in the feed to the fixed bed of the present invention will be about 1.05 to 2.5 preferably 1.4 to 2.0.

In some embodiments the process may be described as comprising the steps of:

(a) feeding (1) a first stream comprising propylene, methyl acetylene and propadiene and (2) a second stream containing hydrogen to a single pass fixed bed reactor wherein a portion of the methyl acetylene and propadiene react with the hydrogen to produce propylene;

(b) feeding the effluent from step (a) to a distillation column reactor into a feed zone;

(c) concurrently in said distillation column reactor
   (i) contacting unreacted methyl acetylene and propadiene with hydrogen in a distillation reaction zone with a hydrogenation catalyst capable of acting as a distillation structure thereby reacting a further portion of said methyl acetylene and propadiene with said hydrogen to form additional propylene, and
   (ii) separating the propylene contained by fractional distillation and (e) withdrawing the separated propylene along with any propane and lighter compounds, including any unreacted hydrogen, from said distillation column reactor as overheads. Optionally the process may include withdrawing any $C_4$ or higher boiling compounds from said distillation column reactor as bottoms. There is no significant loss of propylene from the hydrogenation.

DETAILED DESCRIPTION OF THE PREFERRED EMBODIMENT

Figure 1:
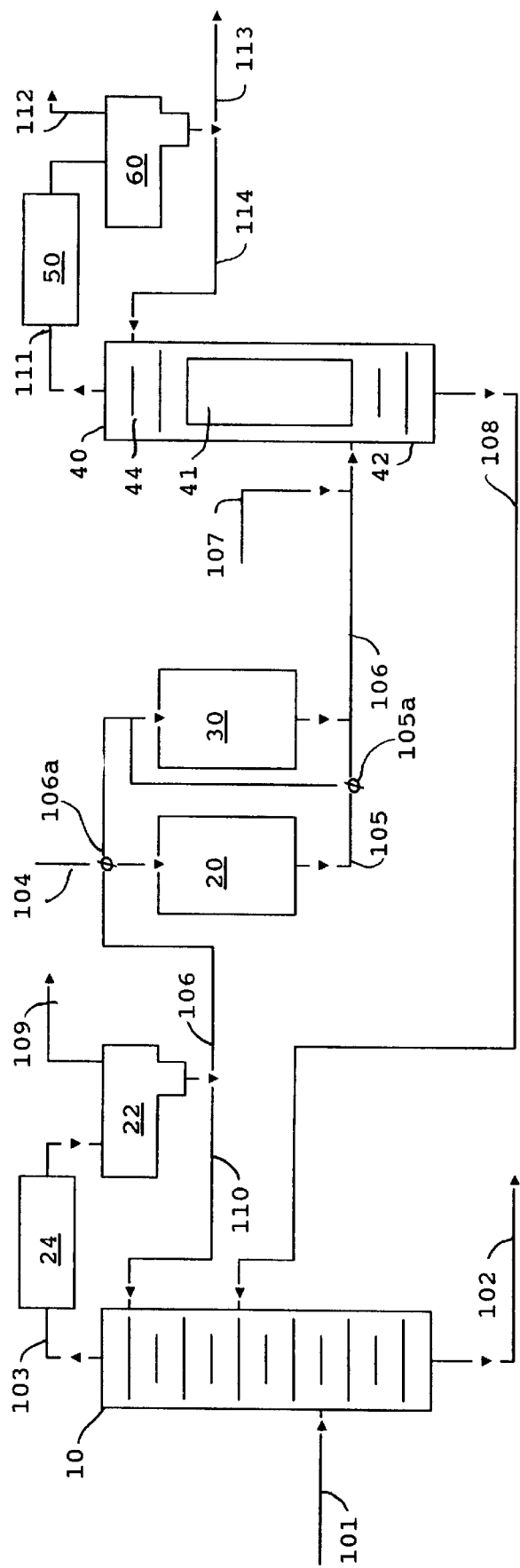
FIG. 1 is flow diagram in schematic form of one embodiment of the invention.

The feed for the instant process may generally be the bottoms from a deethanizer of an ethylene plant. However, any streams which contain propylene contaminated with MAPD would be a candidate for the process. In a particular embodiment of the invention conventional single pass fixed bed reactors, preferably vapor phase, are combined with a distillation column reactor to enhance conversion and selectivity in place of the Green Oil Tower. The advantages of using a distillation column reactor in place of the Green Oil Tower are:

1. Propylene production from the MAPD converters can be increased by a factor of 2.5 thereby increasing unit productivity. The catalytic distillation hydrogenation uses hydrogen more efficiently, thereby providing an operating savings. The attributes of a distillation type reaction, e.g. limited product contact with catalyst and the washing effect of internal reflux, result in less build up of coke on the catalyst and longer reaction times between regenerations for further operations savings.

2. Regeneration frequency is reduced by eliminating the operation of the second bed.

3. The conversion of the Green Oil Tower to catalytic distillation hydrogenation is simple in scope and can be accomplished during a normal plant turnaround. The impact on plant operations is minimal with the potential of simplifying the operation of the unit by eliminating a reactor.

4. Spare reactor vessels can be used for other services.

Catalyst suitable for the present process include 0.05–5 wt % PdO on extruded alumina, such as, 0.3 wt % PdO on ⅛" $Al_2O_3$ (alumina) extrudates, hydrogenation catalyst, supplied by United Catalysts Inc. designated as G68F. Typical physical and chemical properties of the catalyst as provided by the manufacturer are as follows:

TABLE I

| Designation | G68F |
|---|---|
| Form | spheres |
| Nominal size | 3 × 6 Mesh |
| Pd. wt % | 0.3 |
| Support | High purity alumina |

This catalyst may be used in either the single pass reactors or the distillation column reactor (Green Oil Tower). However to be used in the distillation column reactor it must be in a form to also serve as a distillation structure which may, for some distillation columns, be a simple loading of the catalyst. There are several methods and structures available for better performance which are variously described in U.S. Pat. Nos. 4,215,011; 4,439,350; 4,443,559; 5,057,468; 5,189,001; 5,262,012; 5,266,546; 5,348,710; 5,431,890; and 5,730,843 all of which are hereby incorporated by reference. One of the preferred catalyst structures being that described in U.S. Pat. No. 5,730,843.

The structure of U.S. Pat. No. 5,730,843 comprises a rigid frame made of two substantially vertical duplicate grids, spaced apart and held rigid by a plurality of substantially horizontal rigid members and a plurality of substantially horizontal wire mesh tubes mounted to the grids to form a plurality of fluid pathways among the tubes. For use as a catalytic distillation structure, which serves as both the distillation structure and the catalyst, at least a portion of the wire mesh tubes contain a particulate catalytic material. The catalyst within the tubes provides a reaction zone where catalytic reactions may occur and the wire mesh provides mass transfer surfaces to effect a fractional distillation. The spacing elements provide for a variation of the catalyst density and loading and structural integrity.

One typical embodiment of this invention is shown in FIG. 1. It includes a depropanizer 10 to which a $C_3$+ stream containing propane, propylene, MAPD, higher boiling olefins and higher boiling paraffins are fed via flow line 101. The bottoms from the depropanizer contain $C_4$ and higher boiling materials which are taken via flow line 102 for further processing. The overheads from the depropanizer contain the propylene, MAPD, and propane which are taken via flow line 103 and are condensed in condenser 24 and collected in receiver 22 and fed to a via flow line 106 to first vapor phase single pass reactor 20 containing a fixed bed of hydrogenation catalyst. Non condensibles are removed via line 109. Typical operating conditions include 215–315 psig and 100–250° F. A portion of the condensed overheads is returned to the depropanizer 10 as reflux via flow line 110. Hydrogen is added to the reactor via flow line 104. In the reactor 20 a portion of the MAPD is converted to propylene and propane. The first reactor may act as a guard bed to remove catalyst poisons such as arsine, mercury or methanol. The effluent from the first reactor 20 is taken via flow line 105 to second single pass reactor 30 containing a fixed bed of the same or similar hydrogenation catalyst as in reactor 20 wherein additional MAPD is converted to propylene and propane. The effluent from the second reactor 30 is fed via flow line 106 to distillation column reactor 40. Hydrogen as needed is added via flow line 107. This embodiment may also be configured to use the two primary reactors 20 and 30 alternatively by switching the overheads from depropanizer 10 between the reactors by selection of through valve 106a and the corresponding adjustment of the flow line 105 through valve 105a. In this configuration a single reactor serves as the guard bed for the catalytic distillation column, while the catalyst in the other reactor is regenerated or replaced.

In a variant of this embodiment the system can be operated and low pressures, i.e., 90–120 psig. In this case the feed to reactors 20 and 30 may be through line 109. The operating temperature is between 100–250° F. Conversely, in yet another variant the system can be operated at higher pressures in an all liquid mode by pumping the material in the feed line 106 to about 400 psig and heating prior to entering reactors 20 and 30. The temperatures are in the same range.

Distillation column reactor 40 is seen to contain a bed 41 of the same or similar catalyst as in the two reactors 20 and 30 but in a form so as to act as both catalyst and distillation structure. A stripping section 42 containing standard distillation apparatus such as bubble cap trays, sieve trays or packing is provided below the bed 41 to assure that all of the $C_3$'s are removed in the overheads. A rectification section 44 also containing standard distillation apparatus such as bubble cap trays, sieve trays or packing is provided above the bed 41 to assure complete separation. The Green Oil containing unconverted MAPD is removed in the bottoms via flow line 108 and returned to the depropanizer where any $C_3$ material is taken as overheads and recycled to the reactors.

The overheads from the distillation column reactor 40 are taken via flow line 111 and passed through partial condenser 50 where the $C_3$'s are condensed and collected in receiver/separator 60. Uncondensed material, included unreacted hydrogen are taken via flow line 112 with the hydrogen being recycled if desired. The $C_3$ liquid is taken via flow line 113 with a portion being returned to the distillation column reactor 40 as reflux via flow line 114.

Using the processing sequence of this invention the overall selectivity to propylene at start of run is 75%. At end of run the selectivity is about 50%. This is compared to a start of run of about 50% and end of run of 0% for conventional vapor phase converters.

Figure 2:
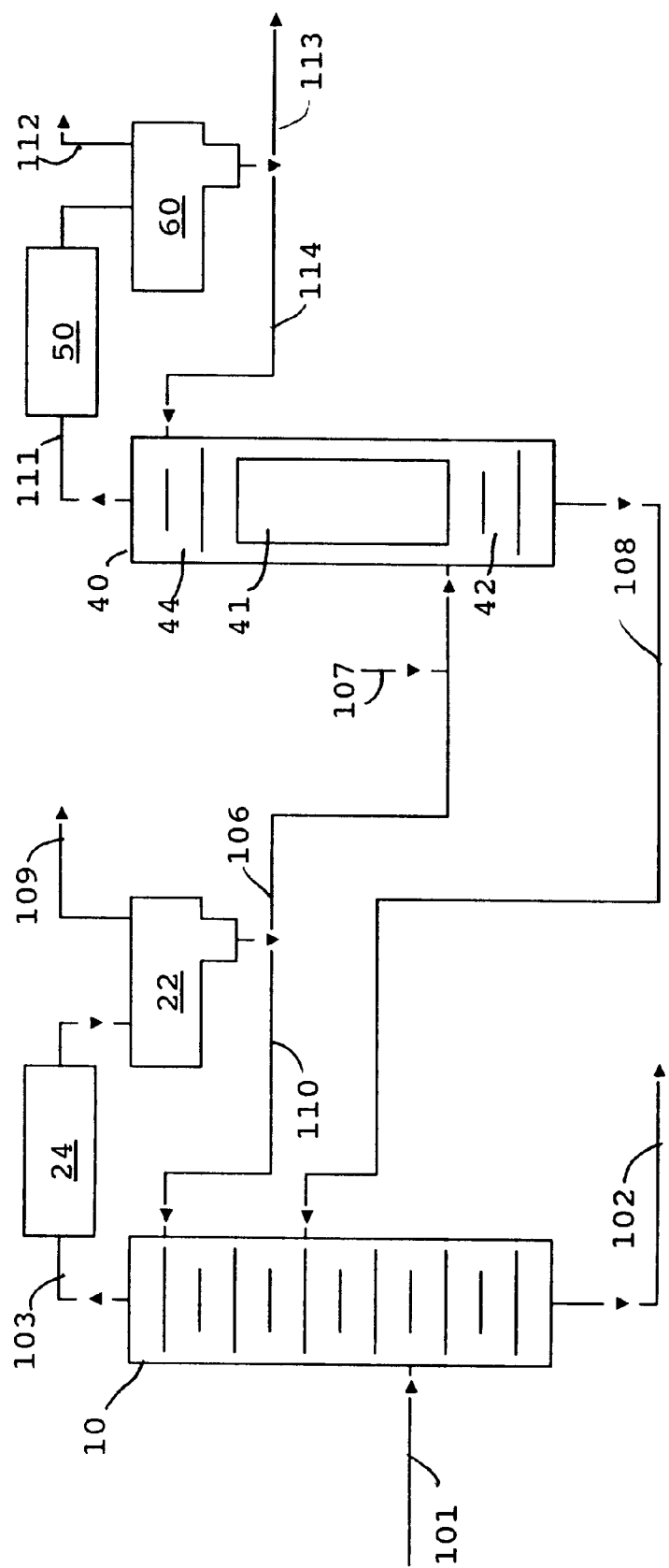
FIG. 2 is flow diagram in schematic form of a second embodiment of the invention.

In a another embodiment of this invention as shown in FIG. 2 the reactors 20 and 30 are deleted. The $C_3$ feed is directly to the distillation column reactor via flow line 106. The depropanizer and distillation column are otherwise identical to FIG. 1.

Figure 3:
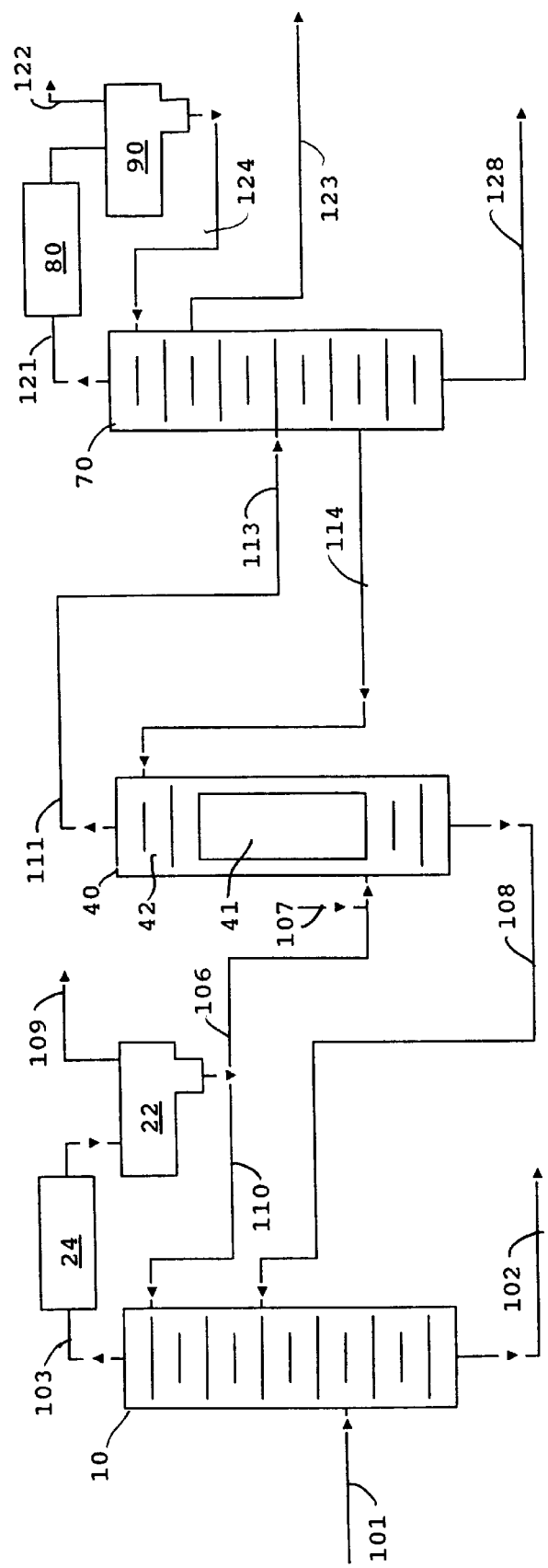
FIG. 3 is flow diagram in schematic form of a third embodiment of the invention.

In another embodiment (shown in FIG. 3) a $C_3$ splitter 70 is positioned after the distillation column reactor 40. The overheads 111 go directly to splitter 70 via flow line 113 and reflux to the distillation column reactor 40 comes from the splitter 70 via flow line 114. Otherwise the operation of the depropanizer 10 and distillation column 40 is the same as in FIG. 2. The overheads from the splitter in flow line 121 contain the lighter material. Any condensible material is condensed in condenser 80 and collected in receiver/separator 90 for reflux to the splitter via flow line 124. Non condensibles are vented flow line 122. Propylene is taken from the column below the overheads via flow 123 and propane is removed as bottoms via flow line 128.

The above embodiments are offered as typical but not limiting illustrations of the flexibility offered by the process and scheme of this invention. Additional variations, configurations and conditions based on the invention would be readily evident to those skilled in the art.

The invention claimed is:

1. A process for the removal of methyl acetylene and propadiene from a propylene rich stream comprising:
    (a) feeding (1) a first stream comprising propylene, methyl acetylene and propadiene and (2) a second stream containing hydrogen to at least one single pass fixed bed reactor containing a first hydrogenation catalyst wherein a portion of the methyl acetylene and propadiene react in vapor phase with the hydrogen to produce propylene;
    (b) feeding the effluent from step (a) to a distillation column reactor into a feed zone;
    (c) concurrently in said distillation column reactor
        (i) contacting unreacted methyl acetylene and propadiene with hydrogen in a reaction zone with a second hydrogenation catalyst thereby reacting said propadiene and methyl acetylene with said hydrogen to form propylene and
        (ii) separating the propylene by fractional distillation; and
    (d) withdrawing the separated propylene along with any propane and lighter compounds, including any unreacted hydrogen, from said distillation column reactor as overheads.

2. The process according to claim 1 wherein said second hydrogenation catalyst is capable of acting as a distillation structure.

3. The process according to claim 1 wherein said hydrogenation catalysts comprise 0.05 to 5.0 wt % palladium oxide on alumina extrudates.

4. The process according to claim 2 wherein hydrogen is contained in said second stream in an amount to provide a mole ratio of hydrogen to said methyl acetylene and propadiene of from 1.05 to 2.5.

5. The process according to claim 2 wherein the overhead pressure of said distillation column reactor is in the range between 90 and 315 psig.

6. The process according to claim 2 wherein the effluent from step (a) is fed to a second single pass fixed bed reactor wherein a further portion of the methyl acetylene and propadiene react with the hydrogen to produce propylene and the effluent from said second single pass fixed bed reactor is fed to step (b).

7. The process according to claim 6 wherein said first single pass fixed bed reactor acts as a guard bed to remove poisons to said hydrogenation catalysts.

* * * * *